(12) United States Patent
Wallach et al.

(10) Patent No.: US 11,994,489 B2
(45) Date of Patent: May 28, 2024

(54) SOLID STATE ION SELECTIVE ELECTRODES

(71) Applicant: Beckman Coulter, Inc., Brea, CA (US)

(72) Inventors: John M. Wallach, Diamond Bar, CA (US); Xihai Mu, Eastvale, CA (US)

(73) Assignee: Beckman Coulter, Inc., Brea, CA (US)

( * ) Notice: Subject to any disclaimer, the term of this patent is extended or adjusted under 35 U.S.C. 154(b) by 11 days.

(21) Appl. No.: 17/144,633

(22) Filed: Jan. 8, 2021

(65) Prior Publication Data

US 2021/0215633 A1 Jul. 15, 2021

Related U.S. Application Data

(60) Provisional application No. 62/960,242, filed on Jan. 13, 2020.

(51) Int. Cl.
  *G01N 27/333* (2006.01)
  *G01N 33/487* (2006.01)

(52) U.S. Cl.
  CPC ..... *G01N 27/333* (2013.01); *G01N 33/48735* (2013.01)

(58) Field of Classification Search
  CPC ........... G01N 27/333; G01N 33/48735; G01N 27/283
  See application file for complete search history.

(56) References Cited

U.S. PATENT DOCUMENTS

| | | | | |
|---|---|---|---|---|
| 3,616,409 A * | 10/1971 | Tosteson | ............ | G01N 27/3335 204/417 |
| 4,211,623 A * | 7/1980 | Ross, Jr. | ............... | G01N 27/333 419/61 |
| 4,431,508 A * | 2/1984 | Brown, Jr. | ......... | G01N 27/3335 204/418 |
| 4,627,893 A * | 12/1986 | Cormier | ............... | G01N 27/403 205/780 |
| 5,505,836 A * | 4/1996 | Miyahara | ........... | G01N 27/3335 204/418 |
| 5,552,032 A * | 9/1996 | Xie | ..................... | G01N 27/3335 205/792 |
| 5,728,290 A * | 3/1998 | Xie | ..................... | G01N 27/3271 204/415 |
| 2002/0038762 A1* | 4/2002 | Eventov | ............ | G01N 27/4035 204/418 |
| 2010/0243480 A1* | 9/2010 | Jiang | .................. | G01N 27/4045 205/786.5 |

(Continued)

FOREIGN PATENT DOCUMENTS

CN 109991293 A * 7/2019
WO WO-2019094966 A1 * 5/2019 ............. D02G 3/404

*Primary Examiner* — Luan V Van
*Assistant Examiner* — Shizhi Qian
(74) *Attorney, Agent, or Firm* — Frost Brown Todd LLP

(57) ABSTRACT

An ion selective electrode ("ISE") assembly may be installed within a sample path of a biological testing system to measure ion concentration within sample fluid flowing through the sample path. A transducer membrane is placed within a housing and positioned to contact the sample path. A threaded portion is advanced into a socket of the housing and forces the membrane against a sealing portion of the sample path to prevent retention of sample fluid within the housing after testing. Sealing may be accomplished without adhesives or sealants and instead relies upon mechanical pressure of the threaded portion.

20 Claims, 7 Drawing Sheets

(56) References Cited

U.S. PATENT DOCUMENTS

2015/0338367 A1* 11/2015 Hu ................. G01N 27/308
                                                            205/780
2016/0223486 A1* 8/2016 Ishige ............. G01N 27/3335

* cited by examiner

SOLID STATE ION SELECTIVE ELECTRODES

BACKGROUND

Various types of tests related to patient diagnosis and therapy can be performed by analysis of the patient's microorganisms, or "microbes." Microbes are microscopic living organisms such as bacteria, fungi, or viruses, which may be single-celled or multicellular. Biological samples containing the patient's microorganisms may be taken from a patient's infections, bodily fluids or abscesses and may be placed in test panels or arrays, combined with various reagents, incubated, and analyzed to aid in treatment of the patient. Automated biochemical analyzers or biological testing systems have been developed to meet the needs of health care facilities and other institutions to facilitate analysis of patient samples and to improve the accuracy and reliability of assay results when compared to analysis using manual operations and aid in determining effectiveness of various antimicrobials.

Such biological testing systems may include the use of ion selective electrodes to determine the ionic concentrations within a biological sample. This may include pumping a sample fluid through channels that pass through or near an ion selective electrode so that a sensing element is exposed to the sample fluid. The sensing element interacts with the fluid sample and generate an electrical voltage which can be measured to determine the concentration of a particular substance in the sample fluid (e.g., sodium, potassium, chloride).

These electrodes and corresponding systems are often expensive, have long response times, and/or require a large sample size. Additionally, many ion selective electrodes can have insufficient sealing between the conductive core and the ion selective membrane. This can create an occurrence, often called "carryover," in which the sample remains within the instrument after analysis such that subsequent analyses of other samples are inaccurate and unreliable.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
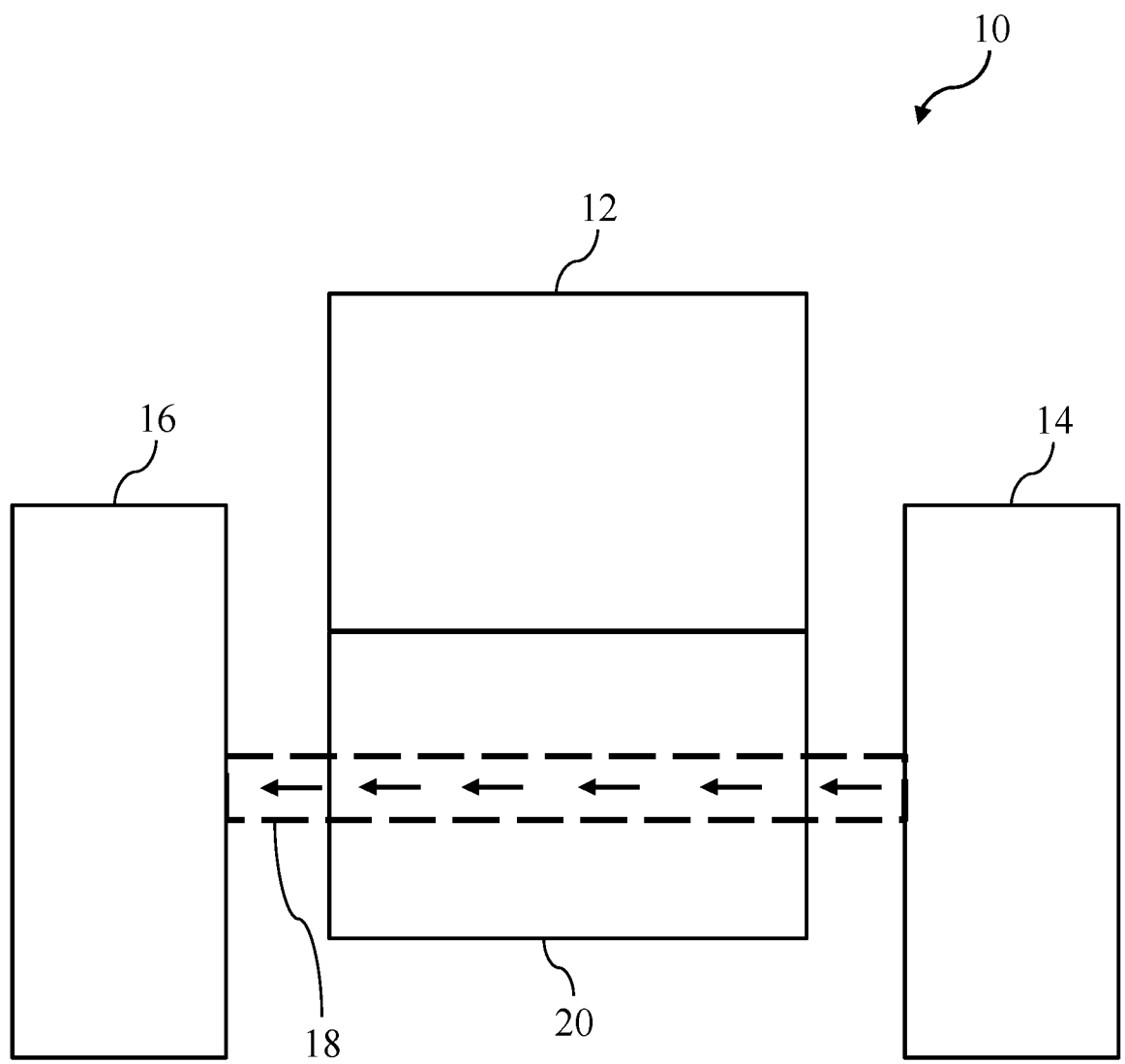
FIG. 1 is a schematic diagram of an exemplary biological testing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

As has been described, many conventional ion selective electrodes ("ISE") are disadvantageous due to various factors. Some conventional ISEs are relatively complex, which can impact cost and reliability. Some conventional ISEs may also use adhesives to affix or seal various components, which can contaminate sample fluid and cause erroneous measurements, or can degrade over time and limit shelf life or increase the risk of carryover. Many conventional ion selective electrodes may also suffer from slow response time and may require exposure to relatively large quantities of sample in order to provide accurate results. The implementations disclosed herein, as well as variations thereof, provide numerous advantages over conventional ISEs.

I. Exemplary Ion Selective Electrode Assembly

FIG. 1 is a schematic diagram of an exemplary biological testing system (10). The biological testing system (10) includes a processor (12) that is configured to operate various components of the biological testing system (10), and that is also configured to receive and produce data associated with the results of biological testing. A sample source (14) is operable by the processor (12) to provide a flow of sample fluid that travels through a sample path (18) and exits at a sample disposal (16). The sample fluid may contain biological samples, reagents, and other fluids and may be prepared prior to being introduced to the biological testing system (10) or, in some implementations, may be mixed and prepared by components of the biological testing system (10). One or both of the sample source (14) and sample disposal (16) may include valves, pumps, and other fluid control components, or positive/negative fluid pressure may be provided by devices upstream or downstream of the sample path (18).

The sample path (18) is a fluid channel having varying lengths, paths, and characteristics depending upon a particular implementation of the biological testing system (10). For example, in some implementations, the sample path (18) may be a single path that transports sample fluid by or through one or more sensing elements (20). In some implementations, the sample path (18) may split or divert a flow of sample fluid to one or more paths. The sensing elements (20) are positioned along the sample path (18) in order to contact the sample fluid as it flows through the sample path (18) and determine one or more characteristics of the sample fluid. This could include, for example, the sample fluid passing through the sensing element (20), or the sensing element (20) projecting into the sample path (18). Determination of sample fluid characteristics may be performed in various ways and, in the case of ISEs, may include the measurement of voltage or other characteristics that is produced as a result of the sample fluid contacting the operative portion of the sensing element (20).

In some implementations, the processor (12) may operate the sample source (14) and/or the sample disposal (16) to control the flow of sample fluid along the sample path (18). As the sample fluid contacts the sensing element (20) a voltage is produced and received by the sensing element (20). The produced voltage may be transmitted to the processor (12), or data indicative of the voltage may be transmitted to the processor (12), and may be used by the processor (12) to produce results indicative of the concentration of ion in the sample fluid (e.g., sodium, potassium, chloride). Such results may then be transmitted to another device, stored on a memory, displayed on a display device, or otherwise used by the processor (12) as will be apparent to those of ordinary skill in the art in light of this disclosure.

Figure 2:
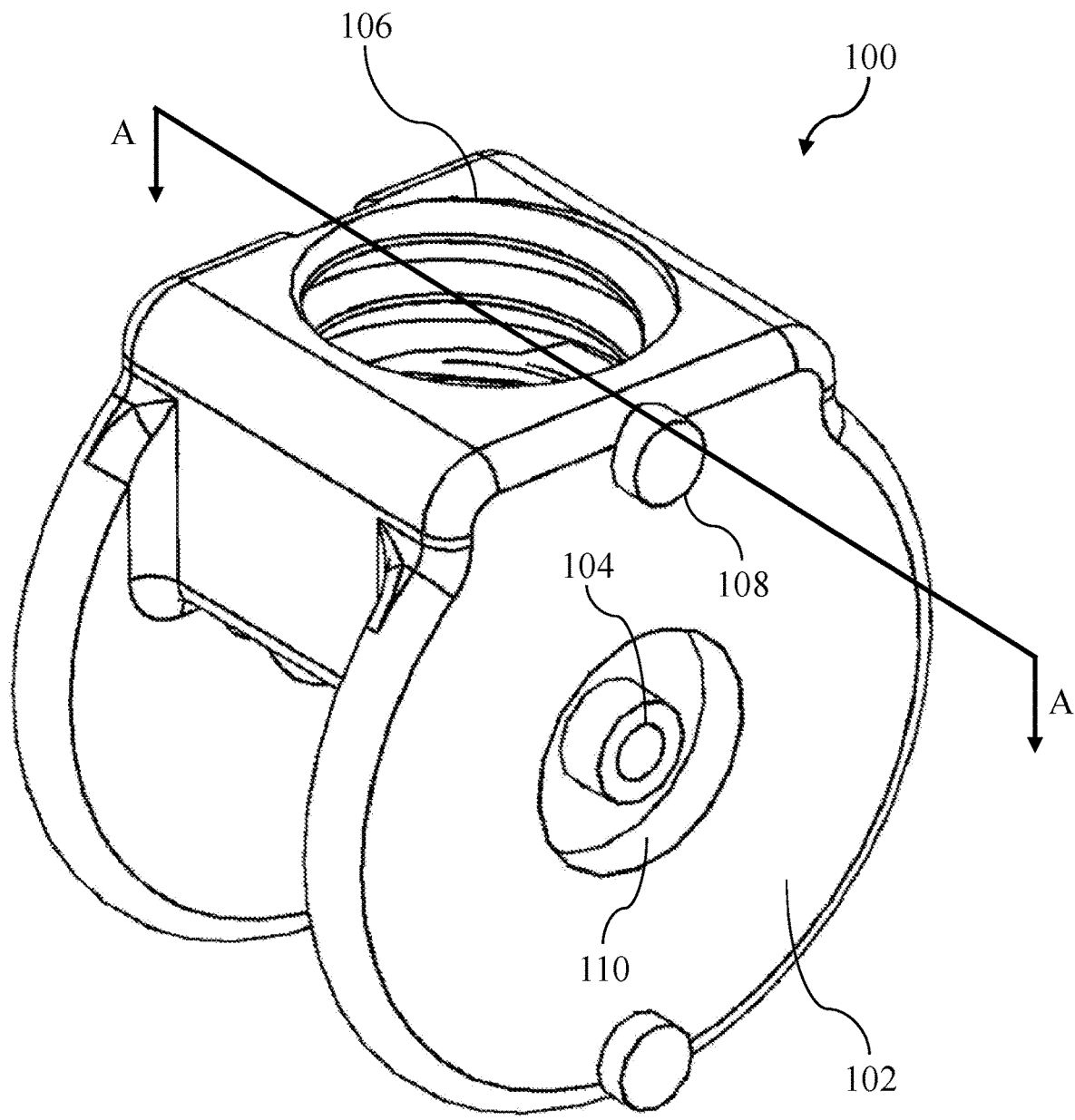
FIG. 2 is a perspective view of an exemplary ion selective electrode assembly with an electrode assembly removed.
Figure 6A:
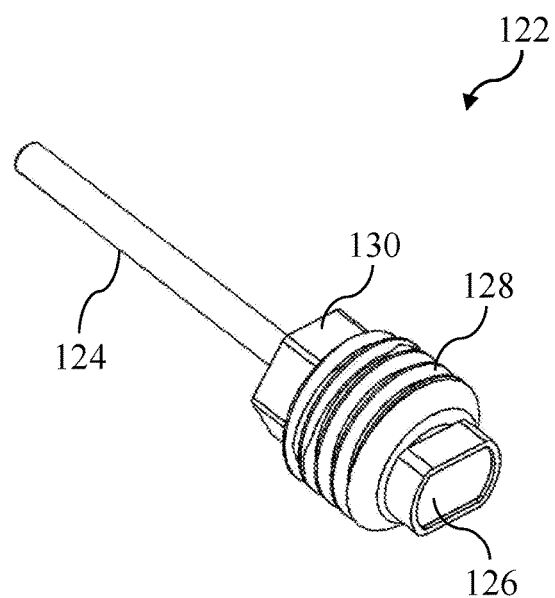
FIG. 6A is a perspective view of an exemplary transducer assembly usable with the ion selective electrode assembly of FIG. 2.
Figure 6B:
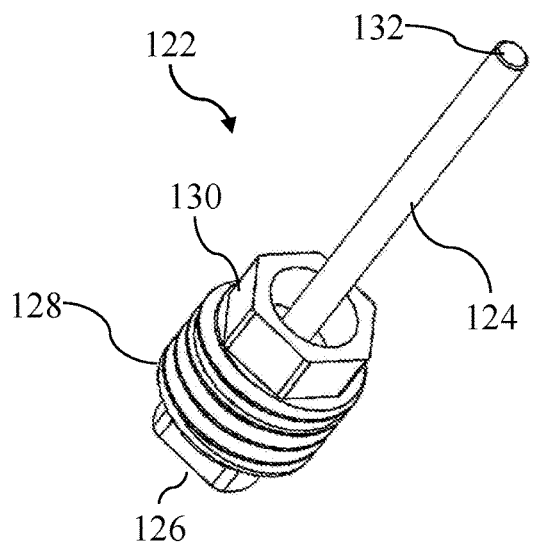
FIG. 6B is an alternate perspective view of the transducer assembly of FIG. 6A.

FIG. 2 is a perspective view of an exemplary ion selective electrode ("ISE") assembly (100) with a sensor, referred to hereinafter as a transducer assembly (122) in this particular embodiment of ISE assembly (100) removed (e.g., a transducer assembly (122) as shown in FIGS. 6A and 6B). The complete ISE assembly (100) may be used with the biological testing system (10) as a sensing element (20). The ISE assembly (100) may be installed within the biological testing system (10) such that the sample path (18) passes through the ISE assembly (100). The ISE assembly (100) includes a housing (102) that shaped and adapted to fit within a receiver portion of the biological testing system (10) in order to integrate the ISE assembly (100) with the sample path (18). The housing (102) may include features to aid in placement, such as a set of mounting tabs (108) which may align and insert into an appropriately sized void in a nearby structures. The housing (102) itself may also include contoured edges, grooves, and other external features that aid in placement and positioning.

A sample input (104) is positioned on the housing (102) such that it is aligned with a source of sample fluid (e.g., such as the sample source (14)) when the ISE assembly (100) is coupled with the biological testing system (10). A sample path seal (110) surrounds the sample input (104), and may couple with an opposing structure when the ISE assembly (100) is installed in the biological testing system (10) in order to aid in sealing between the sample source (14) and the sample input (104). The sample path seal (110) may also aid in proper installation of the ISE assembly (100), similarly to the mounting tabs (108). An transducer assembly socket (106) extends into the housing (102) and is shaped and adapted to receive the transducer assembly (122), as will be described in more detail below.

Figure 3:
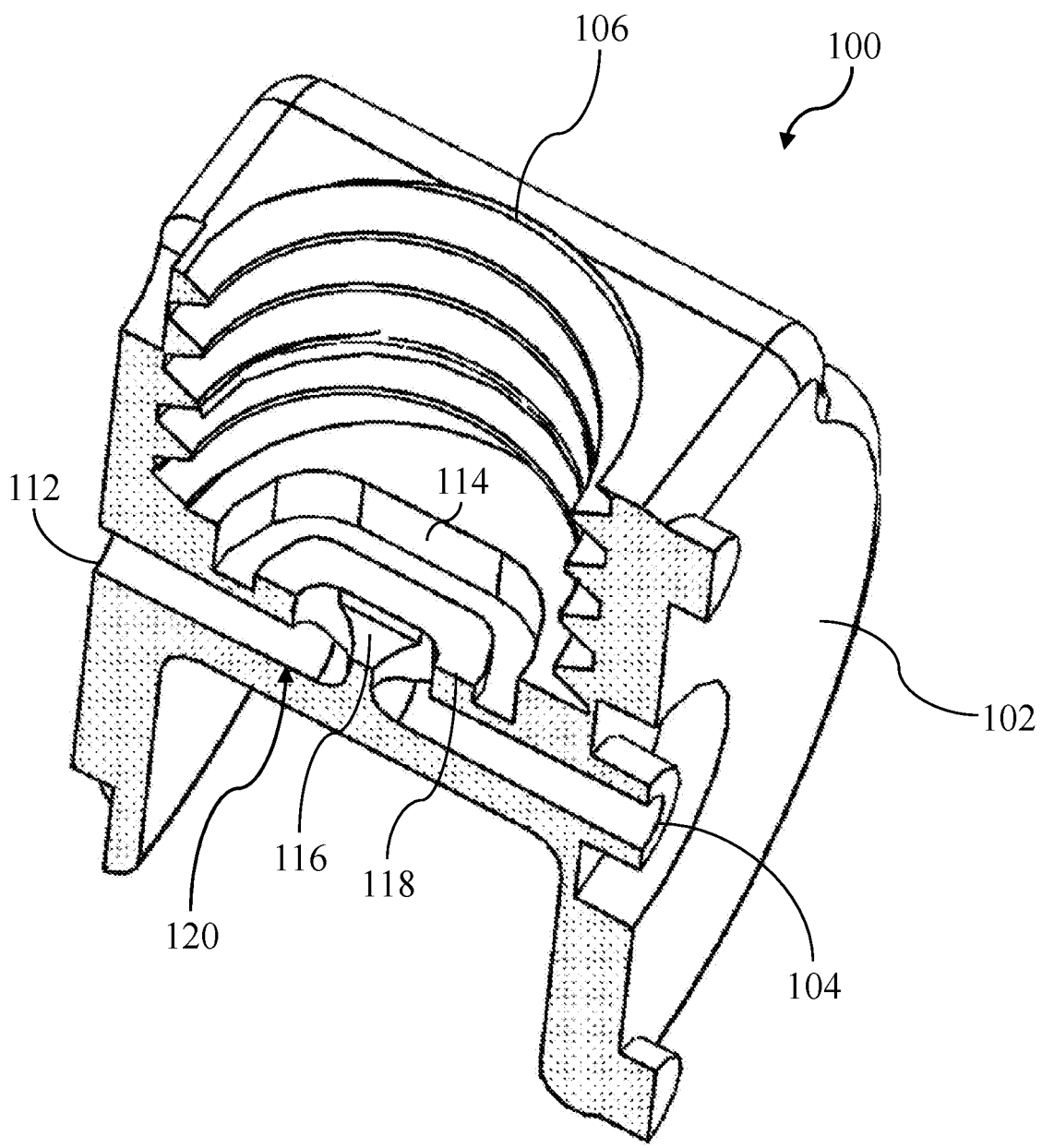
FIG. 3 is a cross sectional view along the line A-A of FIG. 2 of the ion selective electrode assembly.

FIG. 3 is a cross sectional view along the line A-A of FIG. 2 of the ion selective electrode assembly (100). In this view, it can be seen that the sample input (104) passes through the housing (102) and exits at a sample output (112), defining a sample path (120) within the housing (102). The transducer assembly socket (106) is shown as a threaded cavity and can be seen to terminate at a transducer receiver (114). The transducer receiver includes a transducer seal (118) which surrounds a testing portion (116), which may also be referred to as a sensing aperture. The testing portion (116) is an area within the housing (102) where the transducer receiver (114) and the sample path (120) intersect. When the transducer assembly (122) is installed in the housing (102), the operative portion of the transducer assembly (122) may come into contact with sample fluid within the sample path (120) at the testing portion (116), as will be explained in further detail below.

In the view of FIG. 3, it can be seen that sample fluid provided to the sample input (104) will move horizontally through the housing (102), move vertically into and then out of the testing portion (116), and then move vertically through the housing (102) until it exits the sample output (112).

Figure 4:
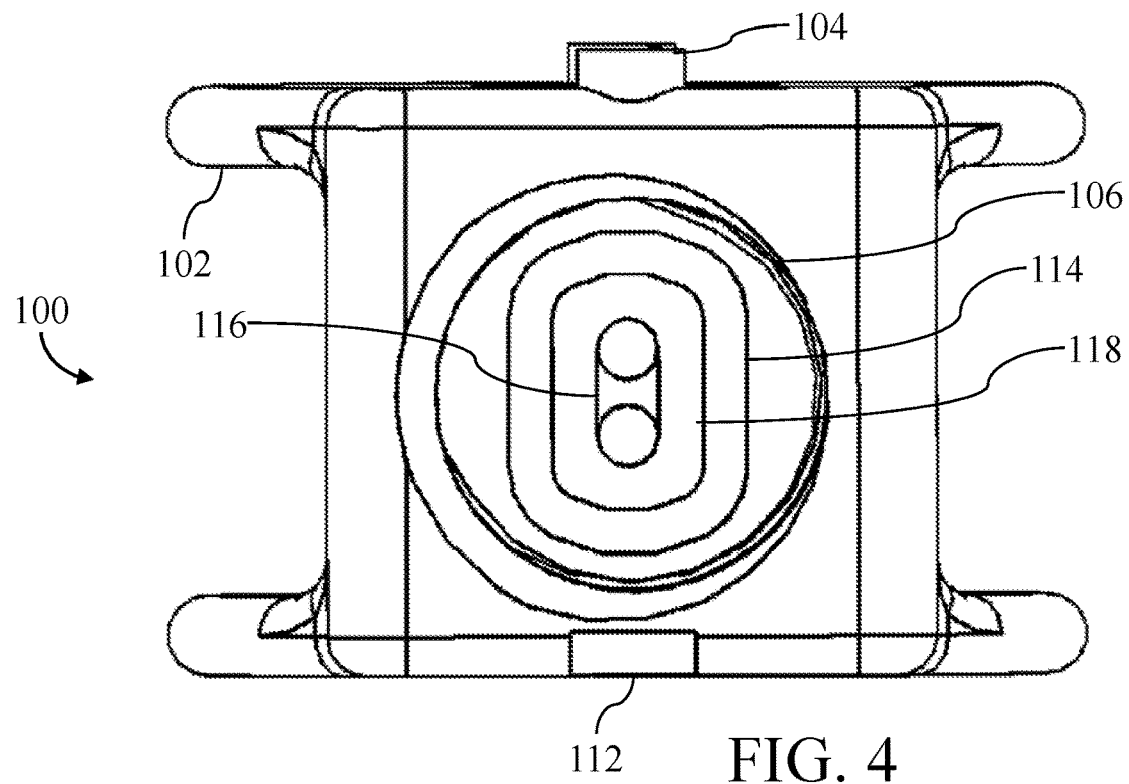
FIG. 4 is a top down view of the ion selective electrode assembly of FIG. 2.
Figure 5:
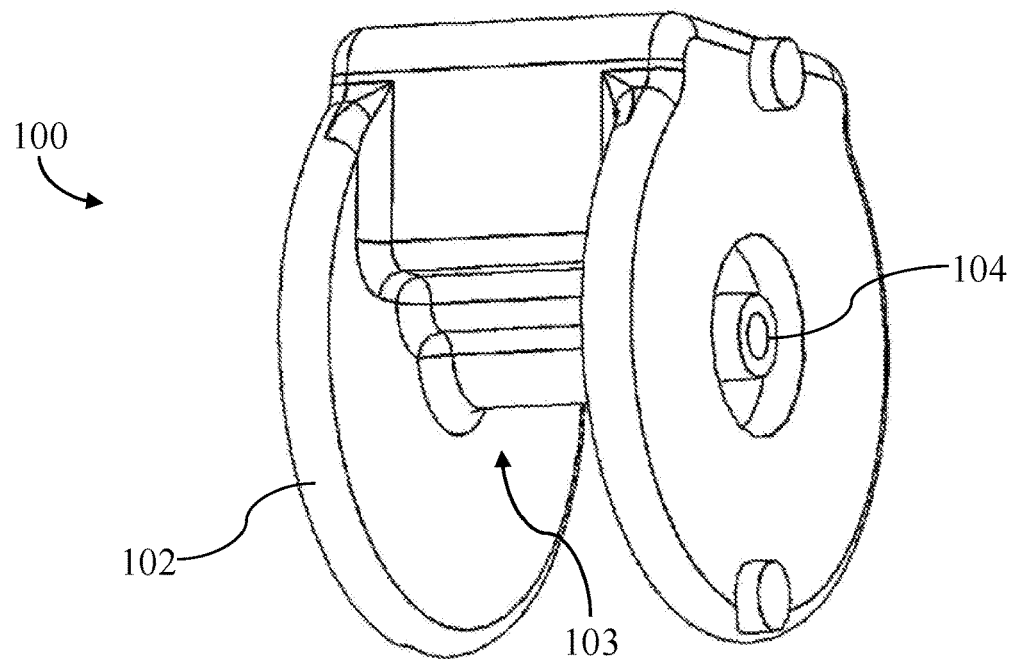
FIG. 5 is an alternate perspective view of the ion selective electrode assembly of FIG. 2.

FIGS. 4 and 5 each show alternate views of the ISE assembly (100). In FIG. 4 the ISE assembly (100) is shown again with the transducer assembly (122) removed, and the area of the transducer receiver (114) can be seen, including the transducer seal (118) and the testing portion (116). FIG. 4 shows additional details of the housing (102), including contoured portions (103) which may be shaped and adapted to aid in positioning of the ISE assembly (100) within the biological testing system (10).

FIGS. 6A and 6B each show perspective views of the transducer assembly (122). The transducer assembly (122) includes transducer (126), a socket plug, hereinafter referred to as a threaded portion (128) in this particular embodiment of ISE assembly (100), an install nut (130), and an electrical contact, referred to hereinafter as a probe (124) in this particular embodiment of ISE assembly (100). The probe (124) terminates at a connector (132) and is conductively coupled to the transducer (126) within the threaded portion (128). When the transducer (126) contacts a fluid sample a voltage is produced and transmitted, via the probe (124) to the connector (132), which itself is adapted to couple with the processor (12) when the ISE assembly (100) is installed within the biological testing system (10). The threaded portion (128) houses a portion of the probe (124) that conductively couples with the transducer (126) and also threads into the transducer receiver (114). The install nut (130) is fixed to the threaded portion (128) and may be gripped with a tool when installing the threaded portion (128) to allow the transducer assembly (122) to be tightly installed in the transducer assembly socket (106).

Figure 7:
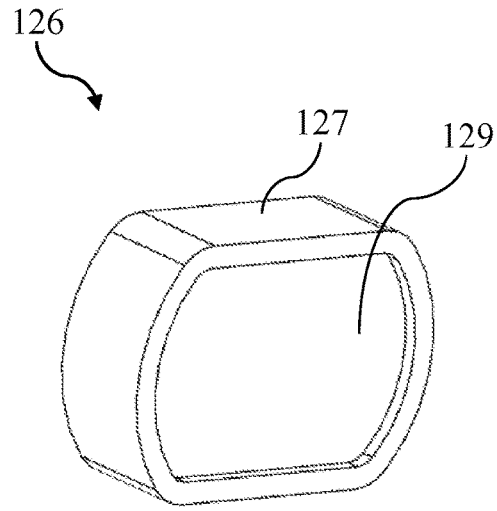
FIG. 7 is a perspective view of an exemplary transducer of the transducer assembly of FIG. 6A.

FIG. 7 shows a perspective view of the transducer (126). The transducer (126) includes a membrane structure, referred to hereinafter as a body (127) in this particular embodiment of ISE assembly (100) and a membrane (129). The membrane (129) may be formed of polymer, glass, crystal, or other appropriate membrane materials, and may be cast or otherwise coupled to the body (127). The body (127) may be formed of a conductive material. For example, in some implementations the body (127) may be formed from a solid graphite material with the membrane (129) cast directly onto the surface of the body (127).

The composition and structure of the membrane (129) may be varied in order to produce transducers capable of measuring various substances, as will be apparent to those of ordinary skill in the art in light of this disclosure. For example, the porosity or thickness of the membrane (129) may be varied depending upon whether the particular membrane is going to measure sodium or potassium. In addition to the membrane (129) allowing the measurement of substances, it is also flexible and aids in sealing the sample path (120) when the transducer assembly (122) is installed in the ISE assembly (100).

Figure 8:
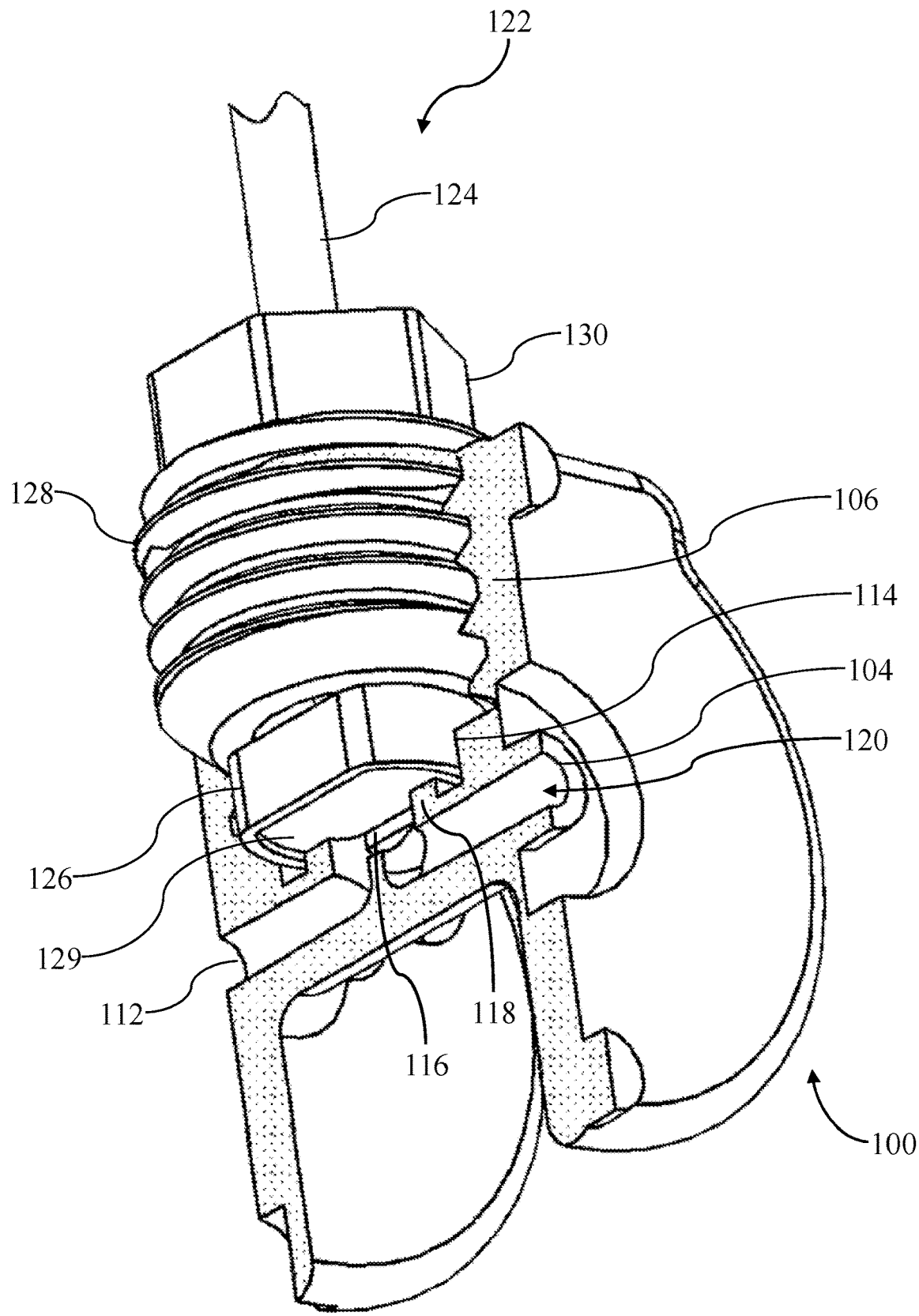
FIG. 8 is a cross sectional view along the line A-A of FIG. 2 of the ion selective electrode assembly including the transducer assembly of FIG. 6.

FIG. 8 is a cross sectional view along the line A-A of FIG. 2 of the ion selective electrode. FIG. 8 illustrates both the fully assembled ISE assembly (100) and the sealing function of the membrane (129). In that figure, the transducer assembly (122) can be seen within the transducer assembly socket (106). While the threaded portion (128) and the transducer assembly socket (128) are shown as a threaded screw-type assembly, it should be understood that the transducer assembly (122) may be fixed within the housing (102) in other ways, such as by friction fit, mechanical latching, and spring release latching, for example.

Below the threaded portion (128), the transducer (126) can be seen seated within the transducer receiver (114) such that the transducer seal (118) is in contact with the membrane (129) of the transducer (126). The ISE assembly (100) may be assembled in the manner shown by, for example, placing the transducer (126) in the transducer receiver (114), and then screwing the threaded portion (128) into the transducer assembly socket (106) by rotating the install nut (130). As the threaded portion (128) is advanced it will contact the backside of the transducer (126) and press it into the transducer seal (118). The membrane (129) will flex as it is pressed against the transducer seal (118) and create a pressure seal against the sample path (120). The threaded portion (128) and install nut (130) may be adapted (e.g., by changing their size or location) to control the depth to which the threaded portion (128) may be advanced in order to allow for suitable pressure to form a seal, while preventing overtightening which may damage the membrane (129). In addition to such structural limitations, other pressure limiting feature may be implemented such as by including a torque-activated slip feature in the install nut (130), providing an inflexible structural contact between the transducer seal (118) and a portion of the transducer (126), or other features as will be apparent to those of ordinary skill in the art in light of this disclosure.

When assembled as shown in FIG. 8, it can be seen that the membrane (129) portion of the transducer (126) is exposed to the testing portion (116) within the sample path (120). As sample fluid flows through the sample path (120) it will contact the membrane (129) allowing for analysis of the sample fluid. This configuration provides a number of advantages. For example, the membrane (129) surface directly integrates with the sample path (120) providing a uniform surface for contacting the sample fluid and preventing carryover or retention of sample fluid between tests. Additionally, the seal between the sample path (120) and the transducer assembly socket (106) is provided by the mechanical force of the threaded portion (128) against the transducer (126), meaning that no adhesives, sealants, or separate sealing features are needed. As a result, there is no risk of contamination from adhesives, and there is no risk of degrading adhesives or sealants eventually failing and reducing shelf life of the ISE assembly (100). The pressure seal provided by the threaded portion (128) is effectively permanent allowing for extended shelf life and may be easily checked or tightened with the install nut (130) prior to or during use.

In some implementations the housing (102) and the transducer assembly socket (106) may be formed of a plastic or polymer, while the threaded portion (128) may be a similar material. Such materials may be selected to aid in achieving a seal between the components, preventing overtightening against the transducer (126), avoiding conductivity from the transducer (126), or in maintaining a seal between the components during a long shelf life in various storage conditions (e.g., as varying temperatures may cause material expansion and reduction for some materials), with such selections being apparent to those of ordinary skill in the art in light of this disclosure.

As an additional advantage, the transducer (126) may be placed directly into the transducer receiver (114) and sealed by placing the threaded portion (128) and tightening the install nut (130). Since the membrane (129) may be cast directly onto the body (127), and since the ISE assembly (100) may be fully assembled without adhesives or other steps, human contact with the membrane (129) may be minimized or entirely avoided. Since contact with the membrane (129) can result in the porous feature being clogged with debris, minimizing such contact and providing a simple assembly of the ISE assembly (100) as illustrated in FIG. 8 may reduce errors and improve the accuracy of test results. As an additional advantage, such implementations provide a solid-state transducer (126) and membrane (129), which may provide benefits in the simplicity, reliability, durability, ease of assembly, and ease of use of the ISE assembly (100). The frequency and extent of maintenance required for the ISE assembly (100) may also be reduced, as there is no need to inspect adhesives or seals or clean or flush carryover contamination from cavities, and there is a reduced need to fully inspect sample paths as compared to ISEs that use a membrane coated sample path.

Varying implementations of the ISE assembly (100) will provide varying contact surface areas between the membrane (129) and the sample path (120). For example, some implementations may have a contact surface area of 0.006 $in^2$, allowing for the overall size of the ISE assembly (100) to be reduced as desired. Accurate measurements with such a contact surface area is possible due to factors such as the solid state design of the transducer (126), the position of the membrane (129) within the sample path (120), the lack of adhesives, solvents, sealants, or other contaminants which may compromise the membrane (129), and other factors. Measurement response time may also be reduced to one second or less, and may be performed with a smaller quantity of sample fluid due in part to the reduced contact surface area and the accuracy at which the membrane (129) can provide results.

As has been discussed, the ISE assembly (100) may be configured to test for the concentration of a particular substance (e.g., sodium, potassium, chloride) by varying the characteristics of the membrane (129). In some implementations, each ISE assembly (100) may test for a single substance, such that the sample path (18) of FIG. 1 may pass through multiple ISE assemblies (100), with each ISE assembly (100) being configured to provide a different measurement. The sample path (18) may pass through the ISE assemblies (100) in sequence or may branch and pass through ISE assemblies (100) in parallel. Other features, variations, and advantages of the ISE assembly (100) exist and will be apparent to those of ordinary skill in the art in light of this disclosure, with some such variations being disclosed and described in further detail below.

II. Exemplary Reference Electrode

Figure 9:
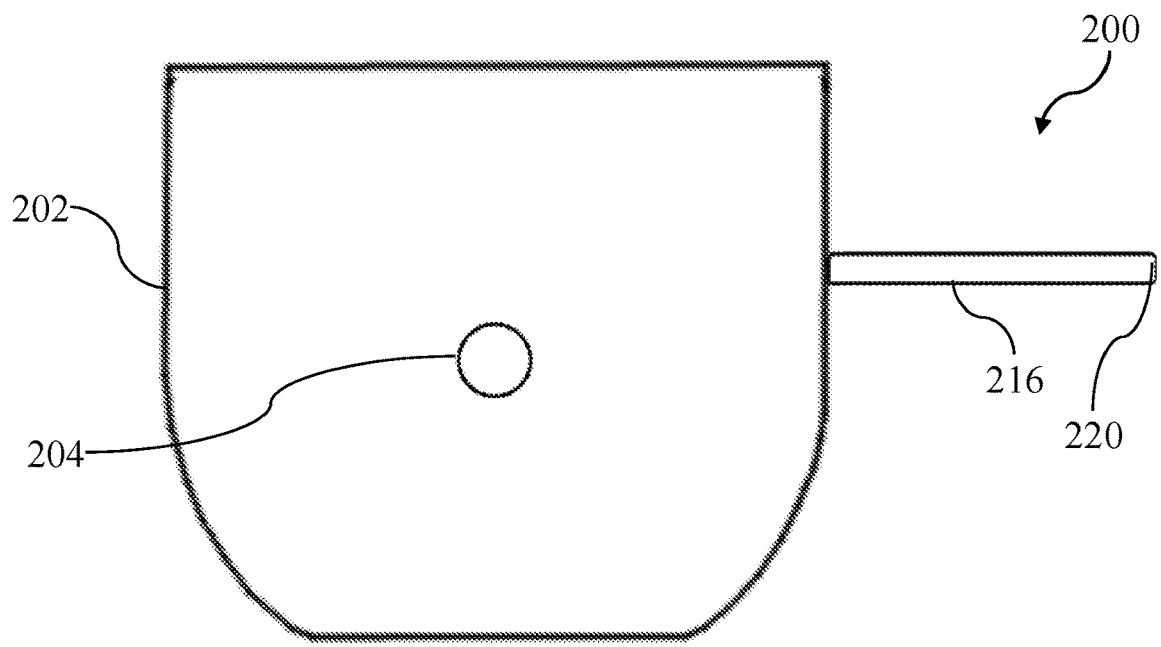
FIG. 9 is a schematic diagram of an exemplary reference electrode.

As has been described, ISEs like the ISE assembly (100) measure concentration of substances in sample fluid based upon a voltage produced during contact. The interpretation of voltage measurements provided by the ISE assembly (100) typically requires a reference voltage. In some implementations, this reference voltage may be provided by a reference electrode. FIG. 9 shows a schematic diagram of an exemplary reference electrode (200) that is implemented and assembled using some of the features of the ISE assembly (100). The reference electrode (200) differs from other ISEs in several ways, including in that it provides a constant voltage measurement during testing and in that the sensing element of the reference electrode (200) does not directly contact the sample path (18).

Figure 10:
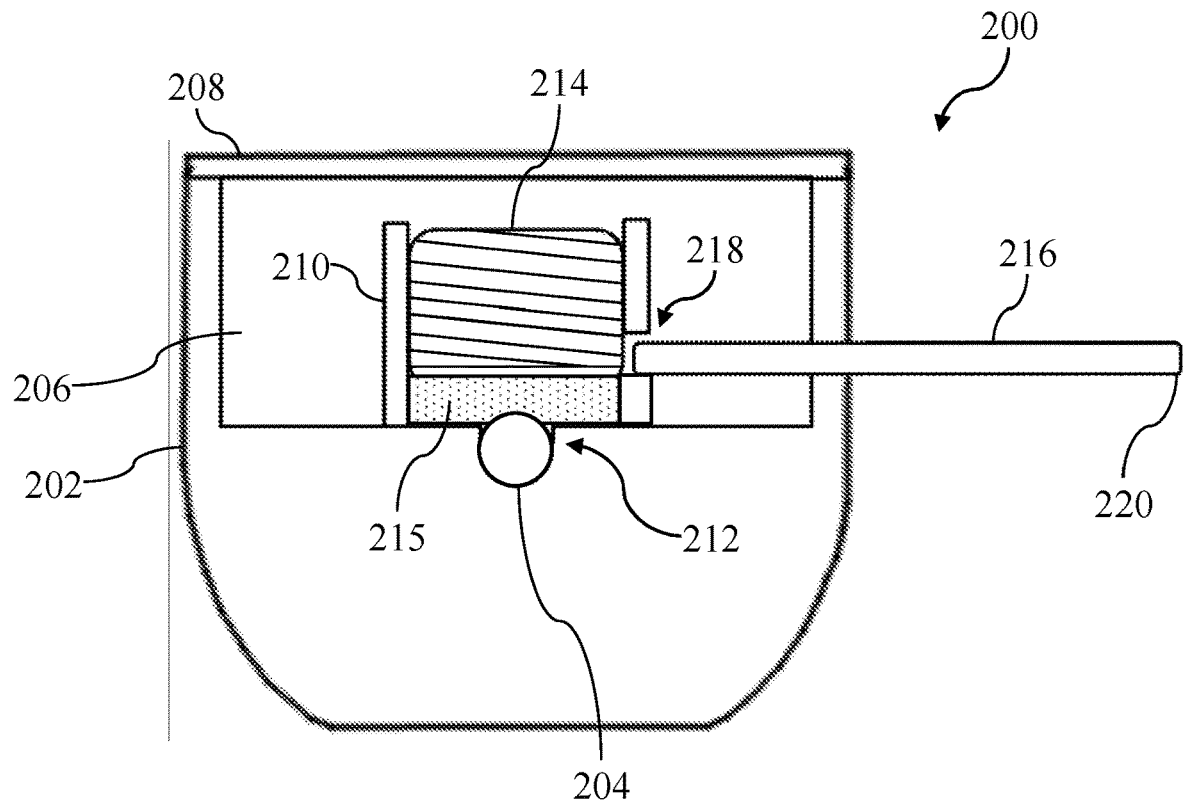
FIG. 10 is a schematic diagram of the reference electrode of FIG. 9 with interior details shown.

As shown in FIG. 9, the reference electrode (200) includes a housing (202) with a sample input (204). A probe (216) partially extends from the housing (202) and includes a connector (220) at a distal end that couples with the processor (12) to provide data or signals indicative of a measured voltage. FIG. 10 is a schematic diagram that illustrates components within the housing (202) of the reference electrode (200). The sample input (204) receives sample fluid when the reference electrode (200) is placed in the sample path (18). Sample fluid travels through a sample path (212) and exits the reference electrode (200) via a sample output (not pictured), as similarly described in the context of the ISE assembly (100). Sample fluid flowing through the sample path (212) will contact a transducer (215). The transducer (215) is sealed against the sample path (212) by a threaded portion (214) that is advanced into a socket (210), as similarly described in the context of the ISE assembly (100).

The housing (202) also includes a reservoir (206) that may be filled with a conductive electrolyte liquid and sealed within the housing (202) by a cap (208). The cap (208) may be pressured sealed onto the housing (202) by screws or other fasteners that attach the cap (208) to the socket (210) or the threaded portion (214). A probe tip (218) at a proximal end of the probe (216) is proximate to but not in contact with the transducer (215). Assembled in this manner, the reference electrode (200) may provide a constant reference voltage to the processor (12) via the connector (220) as the sample fluid contacts the transducer (215). When used in the biological testing system (10), the reference electrode (200) may be paired with one or more ISE assemblies (100) (e.g., in sequence or in parallel, along the sample path (18)) in order to provide a reference voltage usable to determine ionic concentration in the sample fluid.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ion selective electrode comprising: (a) a housing comprising: (i) a sample path passing through the housing, the sample path comprising a sensing aperture, (ii) an electrode socket defined by an opening in the housing, the electrode socket comprising a cavity within the housing accessible from the opening, and (iii) a transducer receiver positioned within the cavity and connected to the sample path via the sensing aperture; (b) a sensor comprising a membrane structure and a membrane, wherein: (i) the membrane structure is configured to position the membrane at the sensing aperture when the sensor is placed in the transducer receiver, so that a liquid solution passing though the sample path contacts the membrane, and (ii) the membrane is configured to produce an electrical potential based upon contact with the liquid solution; (c) a socket plug adapted to fit the electrode socket and bias the membrane against the sensing aperture; and (d) an electrical contact passing through the socket plug and coupled with the sensor, wherein the electrical contact is usable to measure the electrical potential from outside the housing.

Example 2

The ion selective electrode of example 1, wherein the electrical contact comprises an internal contact and an external contact, and wherein: (i) the socket plug is configured to place the internal contact against the membrane structure when coupled with the electrode socket, (ii) the external contact extends from the electrical contact, outside of the housing, and (ii) the internal contact is coupled with the external contact and configured to transfer the electrical potential from the membrane structure to the external contact.

Example 3

The ion selective electrode of any one or more of examples 1 through 2, wherein the socket plug comprises a threading configured to couple the socket plug with the electrode socket and bias the membrane against the sensing aperture as the socket plug is advanced into the electrode socket.

Example 4

The ion selective electrode of example 3, wherein the socket plug is configured to, when threaded into the electrode socket, make contact with the membrane structure and cause the membrane to compress against the sensing aperture and form a fluid impermeable seal between the membrane and the sensing aperture.

Example 5

The ion selective electrode of example 4, wherein the socket plug is configured to, when threaded into the electrode socket, form a fluid impermeable seal between the socket plug and the electrode socket.

Example 6

The ion selective electrode of any one or more of examples 1 through 5, wherein the membrane structure comprises a conductive graphite.

Example 7

The ion selective electrode of example 6, wherein the membrane comprises a solid-state ion selective membrane.

Example 8

The ion selective electrode of example 7, wherein the solid-state ion selective membrane is cast directly onto the conductive graphite.

Example 9

The ion selective electrode of any one or more of examples 1 through 8, wherein a contact surface area defined by the portion of the membrane exposed to the sample path is about 0.006 inches squared.

Example 10

The ion selective electrode of any one or more of examples 1 through 9, wherein the sensor is self-sealing against the sensing aperture when the electrical contact is coupled with the electrode socket.

Example 11

The ion selective electrode of example 11, wherein the sensor and the sensing aperture do not comprise any other sealing features or adhesives.

Example 12

The ion selective electrode of any one or more of examples 1 through 11, wherein the sensor consists essentially of the membrane structure and the membrane.

Example 13

The ion selective electrode of any one or more of examples 1 through 12, wherein the membrane is configured to produce the electrical potential based upon an ionic concentration of an ion in the liquid solution, and wherein the ion is selected from the group consisting of potassium, sodium, and chloride.

Example 14

A method of assembling an ion selective electrode comprising: (a) producing a housing having dimensions selected to fit a desired application, wherein the housing comprises: (i) a sample path passing through the housing, the sample path comprising a sensing aperture, (ii) an electrode socket defined by an opening in the housing, the electrode socket comprising a cavity within the housing accessible from the opening, and (iii) a transducer receiver positioned within the cavity and connected to the sample path via the sensing aperture; (b) producing a sensor by creating a membrane structure having dimensions selected to fit within the transducer receiver, and casting a membrane directly onto the membrane structure, wherein: (i) the membrane structure is configured to position the membrane at the sensing aperture when the sensor is coupled with the transducer receiver, so that a liquid solution passing though the sample path contacts the membrane, and (ii) the membrane is configured to produce an electrical potential based upon contact with the liquid solution; (c) placing the sensor in the transducer receiver; (d) advancing a socket plug into the electrode socket to bias the membrane against the sensing aperture; (e) coupling an electrical contact with the sensor, wherein the electrical contact is usable to measure the electrical potential from outside the housing.

Example 15

The method of example 14, further comprising configuring the membrane to produce the electrical potential based upon an ionic concentration of an ion in the liquid solution, wherein the ion is selected from the group consisting of potassium, sodium, and chloride.

Example 16

The method of any one or more of examples 14 through 15, wherein the membrane structure comprises conductive graphite, and wherein the membrane comprises a solid-state ion selective membrane, further comprising, after producing the sensor, preventing any direct physical contact with the membrane until the sensor is placed within the transducer receiver.

Example 17

The method of any one or more of examples 14 through 15, further comprising, as a result of coupling the electrical contact with the electrode socket by threading the socket plug into the electrode socket: (a) forming a fluid impermeable seal between the socket plug and the electrode socket; and (b) forming a fluid impermeable seal between the membrane and the sensing aperture.

Example 18

The method of example 17, further comprising producing the sensor and forming the fluid impermeable seal between the membrane and the sensing aperture without including any adhesives, and without including any other sealing features in the sensor and the sensing aperture.

Example 19

A reference electrode comprising: (a) a housing comprising: (i) a sample path passing through the housing, the sample path comprising a sensing aperture, (ii) a reservoir within the housing and a cap adapted to seal the reservoir, (iii) an electrode socket within the reservoir, and (iv) a transducer receiver positioned within the electrode socket and connected to the sample path via the sensing aperture; (b) a sensor comprising a membrane structure and a membrane, wherein: (i) the membrane structure is configured to position the membrane at the sensing aperture when the sensor is placed in the transducer receiver, so that a liquid solution passing though the sample path contacts the membrane, and (ii) the membrane is configured to produce an electrical potential based upon contact with the liquid solution; (c) a socket plug adapted to fit the electrode socket and bias the membrane against the sensing aperture; and (d) an electrical contact passing through the housing, into the reservoir, and through the electrode socket such that a proximal tip of the electrical contact is proximate to the sensor socket plug, wherein the electrical contact is configured to transmit an electrical potential from a fluid at the proximal tip to a distal tip outside the housing.

Example 20

The reference electrode of example 19, wherein the socket plug comprises a threading configured to couple the socket plug with the electrode socket and bias the membrane against the sensing aperture as the socket plug is advanced into the electrode socket.

Example 21

The reference electrode of example 20, wherein the socket plug is configured to, when threaded into the electrode socket, make contact with the membrane structure and cause the membrane to compress against the sensing aperture and form a fluid impermeable seal between the membrane and the sensing aperture.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An ion selective electrode comprising:
   (a) a housing comprising:
      (i) a sample path passing through the housing, the sample path comprising a sensing aperture,
      (ii) an electrode socket defined by an opening in the housing, the electrode socket comprising a cavity within the housing accessible from the opening,
      (iii) a transducer receiver positioned within the cavity and connected to the sample path via the sensing aperture, and
      (iv) a transducer seal disposed in the transducer receiver;
   (b) a sensor comprising a membrane structure and a membrane, wherein the membrane is a solid-state ion selective membrane, wherein the membrane is positioned proximate the sensing aperture with the transducer seal directly abutting the membrane when the sensor is placed in the transducer receiver, wherein the membrane produces an electrical potential based upon contact with a liquid solution;
   (c) a socket plug, wherein the socket plug is shaped to be received in the electrode socket, wherein the membrane is biased against the sensing aperture when the socket plug is received in the electrode socket; and
   (d) an electrical contact passing through the socket plug and coupled with the sensor, wherein the electrical contact is usable to measure the electrical potential from outside the housing.

2. The ion selective electrode of claim 1, wherein the electrical contact comprises an internal contact and an external contact, and wherein:
   (a) the internal contact is biased against the membrane structure when the socket plug is disposed in the electrode socket;
   (b) the external contact extends from the electrical contact, outside of the housing; and
   (c) the internal contact is coupled with the external contact and configured to transfer the electrical potential from the membrane structure to the external contact.

3. The ion selective electrode of claim 1, wherein the socket plug comprises a threading shaped to threadably couple the socket plug with the electrode socket and bias the membrane against the sensing aperture as the socket plug is advanced into the electrode socket.

4. The ion selective electrode of claim 3, wherein the socket plug is configured to, when threaded into the electrode socket, abut the membrane structure and cause the membrane to compress against the sensing aperture and form a fluid impermeable seal between the membrane and the sensing aperture.

5. The ion selective electrode of claim 4, wherein the socket plug and the electrode socket form a fluid impermeable seal therebetween when the socket plug is disposed in the electrode socket.

6. The ion selective electrode of claim 1, wherein the membrane structure comprises a conductive graphite.

7. The ion selective electrode of claim 6, wherein the solid-state ion selective membrane is cast directly onto the conductive graphite.

8. The ion selective electrode of claim 1, wherein a contact surface area defined by a portion of the membrane exposed to the sample path is about 0.006 inches squared.

9. The ion selective electrode of claim 1, wherein the sensor is self-sealing against the sensing aperture when the electrical contact is coupled with the electrode socket, wherein a portion of the membrane structure encircles the transducer seal when the sensor is placed in the transducer receiver.

10. The ion selective electrode of claim 9, wherein the sensor and the sensing aperture are free of an O-ring.

11. The ion selective electrode of claim 1, wherein the sensor consists essentially of the membrane structure and the membrane.

12. The ion selective electrode of claim 1, wherein the membrane produces the electrical potential based upon an ionic concentration of an ion in the liquid solution, and wherein the ion is selected from the group consisting of potassium, sodium, and chloride.

13. An ion selective electrode comprising:
(a) a housing, wherein the housing defines a sample path extending therethrough, wherein the sample path includes a testing portion, wherein the housing defines a transducer assembly socket, wherein the housing comprises a transducer seal within the transducer assembly socket;
(b) a transducer assembly, wherein the transducer assembly comprises:
  (i) a threaded portion, wherein the threaded portion includes a first side and a spaced apart second side, wherein the threaded portion is shaped to be removably received in the transducer assembly socket,
  (ii) a transducer, wherein the transducer extends outwardly away from the first side of the threaded portion, the transducer comprising:
    (A) a body formed of a conductive material, wherein the body defines a recessed portion; and
    (B) a solid-state ion selective membrane disposed in the recessed portion of the body, wherein the solid-state ion selective membrane is integrative with the body, wherein the solid-state ion selective membrane produces an electrical potential based upon contact with a liquid solution, wherein the transducer seal is in direct contact with the solid-state ion selective membrane when the threaded portion is received in the transducer assembly socket, and
  (iii) a probe, wherein the probe is conductively coupled with the transducer, wherein the probe extends from the transducer, through the threaded portion, to extend outwardly away from the second side of the threaded portion, wherein the probe conducts the electrical potential from the transducer to outside the housing when the threaded portion is received in the transducer assembly socket.

14. The ion selective electrode of claim 13, wherein the sample path is in fluid communication with the transducer assembly socket.

15. The ion selective electrode of claim 13, further comprising an install nut, wherein the install nut is disposed on the second side of the threaded portion, wherein the probe extends through the install nut.

16. A solid-state ion selective electrode comprising:
(a) a housing comprising:
  (i) a sample path passing through the housing, the sample path comprising a sensing aperture,
  (ii) an electrode socket defined by an opening in the housing, the electrode socket comprising a cavity within the housing accessible from the opening, and
  (iii) a transducer receiver positioned within the cavity and connected to the sample path via the sensing aperture;
(b) a sensor comprising a membrane structure and a solid-state ion selective membrane, wherein the solid-state ion selective membrane is positioned proximate the sensing aperture when the sensor is placed in the transducer receiver, wherein the solid-state ion selective membrane produces an electrical potential based upon contact with a liquid solution;
(c) a socket plug, wherein the socket plug is shaped to be received in the electrode socket, wherein the solid-state ion selective membrane is biased against the sensing aperture when the socket plug is received in the electrode socket; and
(d) an electrical contact passing through the socket plug and coupled with the sensor, wherein the electrical contact is usable to measure the electrical potential from outside the housing.

17. The solid-state ion selective electrode of claim 16, wherein the membrane structure comprises a conductive graphite.

18. The solid-state ion selective electrode of claim 17, wherein the solid-state ion selective membrane is cast directly onto the conductive graphite.

19. The solid-state ion selective electrode of claim 17, further comprising a second fluid impermeable seal, wherein the second fluid impermeable seal is formed between the socket plug and the electrode socket.

20. The solid-state ion selective electrode of claim 16, further comprising a first fluid impermeable seal, wherein the first fluid impermeable seal is formed between the solid-state ion selective membrane and the sensing aperture.

* * * * *